United States Patent [19]
Willging

[11] Patent Number: 4,617,406
[45] Date of Patent: Oct. 14, 1986

[54] PURIFICATION OF TOCOPHEROLS

[75] Inventor: Stephen M. Willging, Minneapolis, Minn.

[73] Assignee: Henkel Corporation, Minneapolis, Minn.

[21] Appl. No.: 700,416

[22] Filed: Feb. 11, 1985

[51] Int. Cl.$^4$ .......................................... C07D 311/72
[52] U.S. Cl. .................................... 549/413; 549/213
[58] Field of Search ................................ 549/413, 213

[56]  References Cited
U.S. PATENT DOCUMENTS
3,338,922  8/1967  Kijima et al. ...................... 549/412
FOREIGN PATENT DOCUMENTS
51-65761  6/1976  Japan ................................. 549/412
55-38347 10/1980  Japan ................................. 549/412

OTHER PUBLICATIONS
Nakamura et al., Chem. Pharm. Bull., 20, 1681 (1972).

Primary Examiner—Nicky Chan
Attorney, Agent, or Firm—Ernest G. Szoke; Robin M. Davis; Patrick J. Span

[57] ABSTRACT

Tocopherol homologues found in a tocopherol-containing feed material can be purified by forming a borate tocopherol ester and then distilling the material containing the esterified tocopherol to remove the materials boiling at temperatures lower than the esterified tocopherol. The borate tocopherol esters remaining after distillation are then reacted with a member selected from the group consisting of: Water, methanol, and ethanol to form tocopherol homologues from the borate tocopherol ester, and the boron by product from this reaction is removed. The tocopherol is then recovered by collecting it, distilling it or by any other convenient collection method.

8 Claims, No Drawings

PURIFICATION OF TOCOPHEROLS

BACKGROUND OF THE INVENTION

Tocopherol compounds, also designated as Vitamin E, are the active components of certain vegetable oils. Vitamin E activity refers to the physiological activity of this group of nutrient materials. Materials having Vitamin E activity all belong to a distinct series of compounds which are all derivatives of chroman-6-ol. These compounds are all tocol derivatives having an isoprenoid $C_{16}$ side-chain, including those compounds having an unsaturated $C_{16}$ side-chain. The term "tocol" is used to mean 2-methyl-2-(4', 8', 12'-trimethyltridecyl)chroman-6-ol. Alpha-, beta-, gamma- and delta-tocopherols are of primary importance for Vitamin E activity, and are commercially isolated from various natural sources. Also important are the enols such as tocomonoenols, tocodienols and tocotrienols which are tocopherol compounds having an unsaturated side-chain. These unsaturated compounds also exhibit Vitamin E activity. Within this description therefore, the terms "tocopherols", "tocopherol compounds" and "tocopherol homologues" are understood to include such unsaturated toco-enol compounds.

Tocopherols, found widely distributed in organic substances, occur in highest concentrations in cereal grain oils, principally in wheat and corn oils, and also in barley and rye. They are also found in vegetable oils such as safflower, soybean, peanut, cottonseed, linseed, sunflower, rapeseed, palm and in other vegetable sources.

In general, tocopherols are widely used for their antioxidant and Vitamin E activity. They are of great value in foods, feeds and medicines for these reasons. Frequently, mixtures of tocopherols are isolated, purified, and methylated to upgrade Vitamin E activity.

Those tocopherol homologues having an unsaturated $C_{16}$ side-chain such as tocotrienol can be hydrogenated and then the beta, gamma, and delta isomers can be upgraded to alphatocopherol Vitamin E activity.

Natural vegetable oils contain small amounts of tocopherols. Such oils as wheat germ oil, soybean oil, and cottonseed oil are considered to be the best sources of Vitamin E. It is desirable for commerical purposes to separate and concentrate tocopherol homologues and to devise methods for separating impurities from tocopherols so that they may be employed for their anti-oxidant and Vitamin E activity.

One method currently used for purifying tocopherols and for the preparation of tocopherol concentrates involves distillation. Distillation, however, fails to separate tocopherols from co-boiling impurities. One method for the preparation of tocopherol concentrates using distillation is reported in U.S. Pat. No. 4,454,329. This distillation process for the purification of tocopherols calls for the esterification of free fatty acids which are present in the feed materials with the tocopherols. The esterified mixture is then distilled and the tocopherols are collected as a distillate. Thus, in this process the fatty acids are esterified and then separated from the tocopherols.

It is worthwhile to note that tocopherol homologues have a phenolic hydroxy group and can therefore be esterified using an acid reactant. Japanese Patent Publication No. 55 (1980-38347) teaches that a borate ester of high reactivity is formed between boric acid and delta-tocopherol. In accordance with this reference, however, the borate delta-tocopherol ester is used as a methylation intermediate for the formation of beta-tocopherol. The intermediate borate delta-tocopherol ester is methylated by a reaction with hexamethyltetramine in the presence of an organic acid catalyst. According to this Japanese publication, the delta-tocopherol ester is a highly reactive intermediate which directs the placement of a methyl group to form beta-tocopherol instead of gamma-tocopherol.

In accordance with the instant invention, borate tocopherol esters can also be formed from the alpha-, beta-, and gamma-tocopherol homologues. The borate esters formed from tocopherol homologues are, moreover, sufficiently stable to be used for the purification of tocopherols. It is therefore an object of the instant invention to provide a process for tocopherol purification using the capacity of alpha-, beta-, gamma-, and delta-tocopherol homologues to form stable borate tocopherol esters. It is a further object of the instant invention to provide a method whereby impurities coboiling with tocopherols can be separated from tocopherol homologues. Other objects will become apparent as this description proceeds.

BRIEF DESCRIPTION

Tocopherol compounds can be purified and separated from co-boiling impurities by the following method. Tocopherols can be purified by a process comprising:

(a) reacting a tocopherol-containing feed material with a member selected from the group consisting of: A boric acid, a boric acid source, an alkoxy boroxine, an alkoxy borate, a phenoxyboroxine and a phenoxyborate to form a borate tocopherol ester;

(b) distilling the product of (a) to leave the borate tocopherol esters in the residue;

(c) releasing the tocopherol from the borate tocopherol ester left after distillation by reacting the borate tocopherol ester with a member selected from the group consisting of water, methanol and ethanol, to form a boron compound and the tocopherol;

(d) removing the boron compound formed in the reaction of (c), and (e) recovering the released tocopherol.

The formation of the tocopherol-borate ester of step (a) also will result in the formation of by products such as water, alcohol, and phenol. In order to maximize the amount of tocopherol purified, the reaction step (a) of the tocopherol present should be substantially complete, and the reformation of the tocopherol be back-reaction prevented. The by-products formed with the tocopherol esters are therefore removed during step (a), thus preventing a back-reaction such as hydrolysis. This can be achieved during step (a) by applying heat to remove these products as the esterification reaction proceeds. Alternatively, the distillation, step (b), can also be used to remove the water alcohol, phenol or other by-products at lower distillation temperatures before the distillation of higher boiling impurities. When these by-products are removed during distillation, the distillation temperatures would be gradually increased to remove higher boiling impurities leaving the borate-tocopherol esters in the residue. Since tocopherolborate esters boil at higher temperatures, impurities which co-boil with tocopherol can be separated in this distillation.

After the completion of the distillation, the tocopherol is then freed from the borate tocopherol ester by reacting it for a sufficient length of time with water, methanol or ethanol. In order to prevent a back reaction with the tocopherol before it can be recovered, the boron compound produced by the reaction between the borate tocopherol ester and the water, methanol and/or ethanol is removed from the released tocopherol. When methanol and/or ethanol has been used, the methyl and/or ethyl borate ester produced is removed by using an azeotropic distillation which removes the borate ester but returns the methanol and/or ethanol to the reaction. This will, advantageously, drive the reaction releasing the tocopherol to completion, thereby maximizing the tocopherol release and recovery. By using an azeotropic distillation, moreover, steps (c) and (d) can proceed simultaneously. When water is used to release the tocopherol from the borate tocopherol ester, the water is contacted with the borate tocopherol ester as a separate phase. The boric acid produced in the reaction will enter the aqueous phase, and can be separated in a phase separation by separating the aqueous layer. Preferably when water is used, and separated as a separate phase, more than one contact is made with the borate tocopherol esters in order to insure complete hydrolysis and boric acid removal.

After the tocopherol is released from the borate tocopherol ester and is separated from the boron compound produced with the tocopherol, the tocopherol is recovered. Since the impurities which otherwise typically co-distill with the tocopherol have been removed by distillation in step (b), the tocopherol can be easily recovered by using another distillation as the recovery method. This will leave other impurities boiling at higher temperatures than the tocopherol in the residue, and the tocopherol can be collected as a distillation product.

Frequently, if substantially all of the tocopherol was released in the reaction of step (c), and substantially all of the boron compound formed in step (c) was removed by step (d), a sufficiently pure tocopherol product will result after step (d), so that the tocopherol can be removed by merely collecting it. This is especially true where there were substantially no impurities present in the tocopherol-containing feed material which boiled at a temperature higher than the tocopherol; or if the tocopherol which could be collected in step (e) was sufficiently pure for a specific use such as antioxidation. Alternative methods which can be applied in step (e) to recover the tocopherol are extraction, adsorption, chromatography and ion exchange.

DETAILED DESCRIPTION

The instant invention can be used to separate alpha-, beta-, gamma- and delta-tocopherol homologues from their organic sources leaving the tocopherols in a more purified form. Even materials as low as 1% by weight tocopherol homologues can be used as starting material for this process. Natural organic sources such as vegetable oils and plant materials can be used as the tocopherol-containing organic feed material. Representative but nonexhaustive examples of such suitable substances are: Safflower, soybean, peanut, cottonseed, linseed, sunflower, rapeseed and palm oils. The starting material can also be taken from other plant sources such as: Palm leaves, lettuce, alfalfa, rubber latex, and a variety of other plant materials.

The present invention can also be used to purify tocopherol homologues from starting materials having higher tocopherol concentrations. Frequently, vegetable oils are used to produce a concentrate that is up to 60% mixed tocopherol. The instant invention can be used to further purify the tocopherols in such materials.

Advantageously, impurities which typically co-distill with the tocopherol homologues can be separated and removed by this process. In fact, even when the starting material is as high as 95% pure tocopherol homologues, the instant invention can be used, especially to separate co-distilling non-tocopherol hydrocarbon impurities from tocopherol thereby achieving a more pure tocopherol product.

In accordance with the instant invention, feed material containing tocopherols is contacted with a sufficient amount of a boric acid, an alkoxyboroxine (meta borates), an alkoxyborate (orthoborate), a phenoxyboroxine (meta borate), a phenoxyborate (orthoborate) and/or a boric acid source whereby a borate tocopherol ester is formed from an esterification reaction.

Unsymmetrical ortho and meta alkoxy tocopherol borate esters can be formed by reacting tocopherol with boron compounds such as: an alkoxyboroxine, an alkoxyborate, a phenoxyboroxine, and a phenoxyborate. Unsymmetrical ortho alkoxy tocopherol borate esters can be formed in situ by reacting boric acid, an alcohol, and tocopherol.

When using an alkoxy and/or phenoxy boroxine and/or borate, the alkoxy and the phenoxy portion must have a molecular weight low enough so that the alcohol produced with the tocopherol borate ester to distill at a temperature lower than the tocopherol so that the reaction can be driven to completion. Removal of the alcohol produced from the phenoxy or alkoxy group can occur during either step (a) or step (b), but it is preferably done during step (a). The alkoxy or phenoxy group of the alkoxy borate, alkoxyboroxine, phenoxyboroxine, and/or phenoxyborate therefore can acceptably have up to 25 carbon atoms; and preferably it will have from about 3 to about 15 carbon atoms.

The maximum boron concentration, provided for by the boric acid, boric acid source, alkoxyboroxine, alkoxyborate, phenoxyboroxine, and the phenoxyboroate, is limited only for reasons of practicality. At high boric acid or boric acid source concentrations, polyborate esters will form. Such polyborate tocopherol esters, however, will still provide tocopherol purification in accordance with the instant invention.

The boron should, however, be present in the minimum amount necessary to insure complete tocopherol esterification so that a maximum amount of tocopherol can be recovered. Thus, there should be a minimum of about $\frac{1}{3}$ mole of boron per mole of tocopherol. Acceptably, the boron concentration can range from a minimum of $\frac{1}{3}$ mole of boron per mole of tocopherol up to 20 moles of boron per mole of tocopherol in the feed material. When sterols are present in the tocopherol containing feed material, there is preferably a large excess of boron available in order to maximize tocopherol esterification. This will allow the formation of both tocopherol borate esters, and borate sterolic esters. The sterolic borate esters can, during step (a), be thermally decomposed before the distillation of step (b). The decomposed sterols can thereafter be removed by distillation during the distillation of step (b). When sterols are present, therefore, the boron concentration provided for can acceptably be at a minimum of about $\frac{1}{3}$ mole of boron per mole of tocopherols and sterols. Preferably, the concentration can range from about ⅓ mole of boron to about 20 moles of boron per mole of tocopherols and sterols combined.

The tocopherol borate esterification reaction will proceed at room temperature. The instant process can, however, be carried out more rapidly at an increased temperature. More acceptably, therefore, the esterification reaction of step (a) is performed at a temperature in the range of from about 40° C. to about 305° C. for a sufficient length of time. A more preferred temperature range is from about 100° to about 225° C., and the most preferred range is from about 160° to about 200° C. At such temperatures, in excess of 100° C., the condensation water produced by the esterification reaction can be substantially eliminated.

In order to retain unreacted tocopherol during esterification, the temperature is maintained under the tocopherol distillation point. Material less volatile than the tocopherol can, however, be removed by using the preferred higher temperatures during esterfication. Thus in the preferred embodiment of the instant invention the distillation of materials boiling at lower temperatures than the tocopherol homologues will occur during esterification. Advantageously, this will also remove the water and/or alcohol formed during esterification which maximizes the formation of the borate tocopherol esters.

If desired, in order to aid in the removal of the water and other volatiles during esterification, the pressure may be lowered. The pressure can therefore range from about atmospheric pressure down to a pressure as low as 1 mm of mercury, or even lower if the temperature is not high enough to distill the tocopherols. Therefore, appropriately, the temperature should be maintained under 250° C. when the pressure is less than 1 mm of Hg so that the tocopherol homologues do not distill before the completion of esterification.

Another option which can be used in accordance with the instant invention which can aid in water or alcohol removal is the addition of a solvent. Advantageously, with the proper solvent, water and/or alcohol can be removed along with the solvent during the distillation step. Additionally, a non-reactive solvent should be used. Acceptable solvents are: Aliphatic hydrocarbon solvents, and aromatics, alcohols and mixtures thereof. Preferred solvents are: xylene, benzene, toluene, alcohols having from about 3 to about 10 carbon atoms, and aliphatics having from about 7 to about 16 carbon atoms.

Removal of esterfication by-products is preferred during esterification since this prevents reformation of the tocopherol by hydrolysis of the borate esters. Moreover as the removal proceeds, the more complete the esterification reaction becomes, and the loss of the tocopherol due to such a premature tocopherol reformation, is prevented.

After esterification is complete, the temperature is increased for distillation step (b); and the impurities boiling at temperatures lower than that of the borate tocopherol esters can then be removed by distillation.

Frequently, after the reaction step (a), there can be undesirable borate solids present in the material. A preferred embodiment of the instant invention will remove these solids by any convenient process, before the distillation of step (b). Preferably, these solids can be removed by filtration, centrifugation, or by using a settling tank. Separating the solids after the reaction of step (a) and before the distillation of step (b) will: Reduce sludge, prolong the life of the distillation equipment, and result in a more pure residue containing the desired tocopherol borate ester after step (b). The solids could instead be removed after step (b) although this is less preferred.

When solids are removed they can either be discarded or reused. The solids are mainly made up of boric acids. They can thus be reused by adding them to the tocopherol-containing feed material for the reaction step (a). In this manner, the solid boric acids can be reused to produce more borate tocopherol esters.

After the formation of tocopherol borate esters, the material remaining which distills at temperatures lower than the borate tocopherol esters can be removed by distillation. The temperature used during the distillation of step (b) should be sufficient to remove substantially all of the impurities boiling at lower temperatures than the tocopherol borate ester. The pressures and temperatures preferably used for distillation will vary depending on the distillation points of the impurities present in the feed material with the tocopherol.

When sterols are present with the tocopherol-containing feed material, sterolic borate esters can form. These sterolic esters are decomposed in either step (a) or step (b) by exposing them to a sufficiently high temperature. Accordingly, temperatures in the range of from about 290° C. to about 305° C. for a sufficient length of time are acceptable. At such temperatures, the sterolic borate esters will decompose and the sterolic decomposition products can be removed during distillation step (b). Alternatively, however, the sterols can be retained with the tocopherol esters for later separation, recovery and use. This subsequent sterolic recovery can be accomplished during the tocopherol recovery of step (e).

A reduced pressure system must be used during the distillation step (b) in order to remove impurities coboiling with tocopherol. For best results, the pressure should be as low as practically possible. Preferably, the pressure should be at a maximum of about 1 mm of mercury (Hg).

After the removal of the impurities in the distillation of step (b), the tocopherol borate esters will remain concentrated in the residue. In order to reform the tocopherol a member selected from the group consisting of: Water, methanol, ethanol or mixtures thereof, is added to the residue for reaction with the borate tocopherol esters. Water, methanol, ethanol or a source of water, methanol and ethanol can be added to the residue remaining after distillation step (b) in a sufficient amount. The amount of water, methanol or ethanol contacting the borate esters to cause the tocopherol release should acceptably be at a minimum of 3 moles of water and/or alcohol per mole of the boron in order to maximize the amount of tocopherol released and available for the recovery step (d). The maximum amount of water, methanol and ethanol used, is limited only for reasons of practicality. Acceptably, the amount of water, methanol and/or ethanol used to contact the borate esters in steps (c) ranges from about 3.5 to about 30 moles per mole of boron to insure a complete tocopherol release.

Methanol and ethanol can be used here to cause the release of the tocopherol from the borate tocopherol ester because of the easy removal of the reaction product that they form; to wit methoxy and ethoxy borate esters formed from the reacting tocopherol borate esters and the methanol and/or ethanol. This removal of the trimethoxy and triethoxy borate esters is accomplished by an azeotropic distillation. The use of the azeotropic distillation will allow both methanol and ethanol to be readded for continued reaction with the borate esters thereby maximizing tocopherol release, while simultaneously the trimethoxy borate ester and triethoxy borate ester is removed. Thus, advantageously, the release of tocopherol can be driven to completion by the use of the azeotropic distillation. Additionally, when the complete tocopherol release is achieved by the complete reaction of the borate tocopherol esters present, the methanol and/or ethanol can be permitted to distill, thereby isolating the tocopherol in the residue.

The reaction with methanol, ethanol and water which releases the tocopherol can acceptably be conducted at ambient temperatures or higher. When water is used, the temperature should be below reflux. This will maximize tocopherol release before water removal. The boric acid formed and excess water can then be separated from the tocopherol product by phase separation. Preferably, the tocopherol product isolated is washed with water and/or distilled to insure a complete removal of boric acid.

If temperatures greater than the boiling point of water are desired, pressure can be added to increase the reflux point. With increased pressure, the temperature can be allowed to go as high as 300° C.

After the reformation of tocopherol from the borate tocopherol esters in step (c), and the removal of the boric acid, or trimethyl and/or triethyl borate ester in step (d), the tocopherol is recovered in step (e).

If the tocopherol is sufficiently pure after step (d) for any particular use, it can be recovered by collecting it. Frequently, highly pure tocopherol can be obtained in the application of step (a) through (d). This is especially true if (1) the tocopherol-containing feed material used contained substantially no impurities which boiled at temperatures higher than tocopherol or higher than the highest distillation temperature of step (b) if that temperature was greater; (2) if the release of the tocopherol in step (c) was substantially complete; and (3) if the removal of the boron compound in step (d) was substantially complete. In such a case, the tocopherol is recovered by collecting it from its vessel.

If, however, further purification is necessary, methods which can be used to recover the tocopherol are: Chromatography, extraction, ion exchange and distillation. Of these, the most preferred is distillation. Such a step will separate tocopherol from the impurities boiling at a higher temperature than the tocopherol. The tocopherol is, in this case, recovered as a distilled product.

The process of the instant invention will be more fully understood from the examples which follow. These examples are intended to clarify and demonstrate the instant invention and not to limit it. All parts and percentages are by weight unless otherwise specified.

EXAMPLES

Example 1

500 grams of a mixed tocopherol concentrate which was 72% by weight tocopherol homologues was heated with 55 grams of ortho boric acid ($H_3BO_3$) up to 200° C. over a 2 hour period under a vacuum of 2-3 mm of Hg. The resulting mixture was then cooled to 140° C. and was filtered through a glass wool plug.

The filtered material was then wiped-film distilled using a 2 inch still. The wiped-film still wall temperature was 250° C., and the pressure maintained within the wiped-film still was maintained between 0.4 and 0.2 mm of mercury (mm of Hg) while the feed rate of the material being distilled was maintained at 13 ml per minute (ml/min.). The distillate obtained from this distillation was 10% by weight tocopherol homologues (3% of yield) and 88.7% by wt were coboiling impurities.

The residue from the above distillation was refluxed with 300 grams of water for 30 minutes. The water phase remaining after this was removed and the organic material left was washed twice with 300 grams of hot water. The organic material was then placed under a vacuum of 2-3 mm of Hg to remove residual water.

After the residual water was removed by vacuum, the resulting product was distilled in a wiped-film still to give a tocopherol product that was 96% by wt tocopherol.

Example 2

Mixed tocopherol/orthoborate esters were formed in situ by reacting 2 kg of n-butanol, and 150 g (grams) of orthoboric acid in the presence of 1 kg of a tocopherol concentrate which was 72% by wt total tocopherols. The concentrate had been derived from soya oil. This mixture was heated at 100° C. for 2 hours with the azeotropic removal of water. Excess n-butanol was removed by distillation at atmospheric pressure. The excess tri-n-butylborate was removed by vacuum distillation.

The resulting reaction product was then distilled using a wiped-film distillation under a vacuum of 0.4 mm of Hg at 260° C. The distillate collected contained the impurities while the residue consisted of mixed tocopherols/n-butanol ortho borate esters.

Tocopherol was liberated from the esterification product contained in the residue by hydrolyzing the mixed tocopherol/n-butanol orthoborate esters in octane at 100° C. with water for 30 minutes. After the removal of the octane and the water, the hydrolyzed product was wiped-film distilled. Tocopherols were recovered in the distillate as 92% pure tocopherol homologues for a yield of 90%.

What is claimed is:

1. A process for the purification of tocopherol comprising:
   (a) reacting the tocopherol in a tocopherol-containing feed material with a member selected from the group consisting of: boric acid, an alkoxy boroxine, an alkoxy borate, a phenoxyboroxine, and a phenoxyborate to form a borate tocopherol ester;
   (b) distilling the product of (a) to leave the borate tocopherol esters in the residue;
   (c) releasing the tocopherol from the borate tocopherol ester left after distillation by reacting the borate tocopherol ester with a member selected from the group consisting of: water, methanol and ethanol to form the tocopherol and a boron compound;
   (d) removing the boron compound formed by the reaction of the water, methanol and ethanol in step (c), and then
   (e) recovering the released tocopherol after step (d).

2. A process described in claim 1 wherein the reaction of step (a) is at a temperature in the range of from about 40° to about 305° C.

3. A process as described in claim 1 wherein an excess amount of water is used in step (c) to release the tocopherol, thereby forming boric acid.

4. A process as described in claim 1 wherein the tocopherol is released from the borate tocopherol ester by reacting it in step (c) with a member selected from the group consisting of: Methanol and ethanol.

5. A process as described in claim 3 wherein the boric acid formed in step (c) is removed in step (d) by an aqueous phase separation.

6. A process as described in claim 4 wherein the boron compound formed in step (c) is removed by using an azeotropic distillation.

7. A process as described in claim 6 wherein the amount of methanol and ethanol used in step (c) is from about 3.5 to about 30 moles per mole of boron present.

8. A process as described in claim 7 wherein the tocopherol is recovered as a distillation product.

* * * * *